United States Patent
Duerig et al.

(10) Patent No.: US 6,503,272 B2
(45) Date of Patent: Jan. 7, 2003

(54) STENT-BASED VENOUS VALVES

(75) Inventors: Thomas W. Duerig, Fremont, CA (US); Andreas Melzer, Muehlheim-Ruhr (DE)

(73) Assignee: Cordis Corporation, Miami Lakes, FL (US)

( * ) Notice: Subject to any disclaimer, the term of this patent is extended or adjusted under 35 U.S.C. 154(b) by 58 days.

(21) Appl. No.: 09/813,586

(22) Filed: Mar. 21, 2001

(65) Prior Publication Data

US 2002/0138135 A1 Sep. 26, 2002

(51) Int. Cl.7 .................................................. A61F 2/06
(52) U.S. Cl. ....................................................... 623/1.24
(58) Field of Search ............................. 623/1.24, 1.15, 623/1.3, 1.31; 606/200

(56) References Cited

U.S. PATENT DOCUMENTS

| | | | |
|---|---|---|---|
| 5,332,402 A | | 7/1994 | Teitelbaum |
| 5,358,518 A | | 10/1994 | Camilli |
| 5,500,014 A | | 3/1996 | Quijano et al. |
| 5,609,626 A | | 3/1997 | Quijano et al. |
| 5,662,713 A | | 9/1997 | Andersen et al. |
| 5,695,499 A | | 12/1997 | Helgerson et al. |
| 5,824,061 A | | 10/1998 | Quijano et al. |
| 5,840,081 A | * | 11/1998 | Andersen et al. .......... 623/2.36 |
| 5,843,171 A | | 12/1998 | Campbell et al. |
| 5,855,597 A | | 1/1999 | Jayaraman |
| 5,855,601 A | | 1/1999 | Bessler et al. |
| 5,876,445 A | | 3/1999 | Andersen et al. |
| 5,938,696 A | | 8/1999 | Goicoechea |
| 5,957,949 A | | 9/1999 | Leonhardt et al. |
| 5,997,573 A | | 12/1999 | Quijano et al. |
| 6,068,638 A | | 5/2000 | Makower |
| 6,071,277 A | | 6/2000 | Farley et al. |
| 6,086,610 A | | 7/2000 | Duerig et al. |
| 6,254,564 B1 | * | 3/2001 | Wilk et al. ....................... 604/9 |
| 6,245,102 B1 | * | 6/2001 | Jayaraman .................. 623/1.15 |
| 6,299,637 B1 | * | 10/2001 | Shaolian et al. ............ 623/1.24 |
| 325,824 A1 | * | 12/2001 | Limon ......................... 623/1.2 |
| 6,342,067 B1 | * | 1/2002 | Mathis et al. ............... 623/1.15 |
| 6,440,164 B1 | * | 8/2002 | DiMatteo et al. ........... 623/1.24 |
| 2002/0032481 A1 | | 3/2002 | Gabbay |

FOREIGN PATENT DOCUMENTS

| | | |
|---|---|---|
| EP | 0 928 606 | 7/1999 |
| WO | WO/0047136 | 8/2000 |
| WO | WO/0047139 | 8/2000 |
| WO | WO/0149213 | 7/2001 |

OTHER PUBLICATIONS

2002/032481, A1, Gabbay, 03/2002

* cited by examiner

*Primary Examiner*—David H. Willse
*Assistant Examiner*—Suzette J. Jackson
(74) *Attorney, Agent, or Firm*—Carl J. Evens (57) ABSTRACT

An artificial venous valve which incorporates a stent having one or more of the elements comprising its frame deformed inwardly towards its center and a biocompatible fabric attached to the one or more elements is utilized to replace or supplement incompetent or damaged venous valves. The elements are deformed and the fabric attached in such a way as to form valve flaps, which when there is no pressure differential on opposite sides of the flaps, substantially occludes the lumen of the vessel into which the artificial valve has been deployed. When there is a pressure differential, albeit slight, due to the pumping of the heart, the flaps easily open and allow blood to flow therethrough while substantially preventing backflow.

19 Claims, 10 Drawing Sheets

STENT-BASED VENOUS VALVES

BACKGROUND OF THE INVENTION

1. Field of the Invention

The present invention relates to medical devices, and more particularly to stent-based venous valves.

2. Discussion of the Related Art

The vertebrate circulatory system comprises three major types of blood vessels; namely, arteries, capillaries and veins. Arteries carry oxygen-rich blood from the heart to the other organs and veins carry oxygen-depleted blood from the organs back to the heart. The pulmonary vein is an exception in that it carries oxygen-rich blood from the lungs to the heart. When an artery enters an organ, it divides into a multiplicity of smaller branches called arterioles. Metarterioles are small vessels that link arterioles to venules, which are the multiplicity of smaller vessels that branch from veins. Capillaries branch off from and are connected to metarterioles. Capillaries also interconnect with one another forming long and intricate capillary networks. After blood supplied by arteries courses through an organ via a capillary network, blood enters the venules which eventually merge into veins and is transported back to the heart.

Given the nature of the circulatory system, it is easy to understand that blood pressure in arteries is much greater than in veins. To compensate for the much lower blood pressure, veins comprise low flow resistance tissues and venous valves. The primary benefit of venous valves is their ability to limit the backflow of blood traveling through the venous portion of the circulatory system. Numerous venous valves are located throughout the veins, thereby ensuring that the blood travels through the veins and towards the heart.

The normally low blood pressure in the venous portion of the circulatory system is supplemented by the contraction of skeletal muscles. Essentially, the contraction of the muscles compresses and drives the blood through the veins. The venous valves check the backflow of blood through the veins, thereby ensuring that blood is driven back to the heart. The backflow checking function performed by the venous valves also minimizes the effect of a sudden increase in blood pressure caused, for example, by heavy exertion. In addition, venous valves also evenly distribute blood in the veins by segregating portions of blood flowing through the venous portion of the circulatory system. Any damage to the venous valves disrupts the normal flow of blood.

Venous valves are particularly important in the lower extremities. The venous system in the lower extremities generally consists of deep veins and superficial veins, which lie just below the skin surface. The deep and superficial veins are interconnected by perforating veins. Blood generally flows upwards through the legs towards the heart and from the superficial to deep veins. The venous valves are situated in the deep, superficial and perforating veins to ensure the normal direction of blood flow.

Venous valves can become incompetent or damaged by disease, for example, phlebitis, injury or the result of an inherited malformation. Incompetent or damaged venous valves usually leak blood. The backflow of blood passing through leaking venous valves may cause numerous problems. As described above, blood normally flows upwards from the lower extremities, and from the superficial to deep veins. Leaking venous valves allow for blood regurgitation reflux causing blood to improperly flow back down through the veins. Blood can then stagnate in sections of certain veins, and in particular, the veins in the lower extremities. This stagnation of blood raises blood pressure and dilates the veins and venous valves. The dilation of one vein may in turn disrupt the proper functioning of other venous valves in a cascading manner. The dilation of these valves may lead to chronic venous insufficiency. Chronic venous insufficiency is a severe form of venous disease and is a pathological condition of the skin and subcutaneous tissues that results from venous hypertension and prolonged stasis of venous blood due to valvular incompetence both of a primary nature and of a secondary nature following past illnesses of the venous subsystem. Chronic venous insufficiency progresses through various stages of symptom severity which in order of severity include venous flare, edema, hyper-pigmentation i.e. discoloration of the skin, eczema, induration i.e. thickening of the skin, and ulcers. If neglected, chronic valve insufficiency may necessitate amputation of the neglected limb.

Numerous therapies have been advanced to treat symptoms and to correct incompetent valves. Less invasive procedures include compression, elevation and wound care. Compression involves the use of elastic stockings to compress the affected area. Compression is a conservative therapy and is typically effective in a majority of cases. However, the elastic stockings are uncomfortable and expensive. Continuous elevation is frequently used to treat venous ulcers. Elevation of the affected limb improves venous return, reduces the discomfort of ulcers, and encourages healing. Elevation, however, is contraindicated in patients with cardiopulmonary insufficiency. Wound care involves the use of antibiotics and antiseptics. Topical antibiotics and antiseptics are frequently utilized to treat ulcers. Zinc paste bandages have been a primary dressing for over a century. However, these treatments tend to be somewhat expensive and are not curative. Other procedures involve surgical intervention to repair, reconstruct or replace the incompetent or damaged venous valves.

Surgical procedures for incompetent or damaged venous valves include valvuloplasty, transplantation, and transposition of veins. Valvuloplasty involves the surgical reconstruction of the valve. Essentially, valvuloplasty is a procedure to surgically modify the venous valves to "tighten" them. Transposition of veins involves surgically bypassing sections of veins possessing the incompetent or damaged valves with veins possessing viable valves. Transplantation involves surgically transplanting one or more of a patient's viable valves for the incompetent or damaged valve. A more detailed discussion of these surgical procedures is given in "Reconstruction of Venous Valves", R. Gottlub and R. Moy, Venous Valves, 1986, Part V, section 3.

The above-described surgical procedures provide somewhat limited results. The leaflets of venous valves are generally thin, and once the valve becomes incompetent or destroyed, any repair provides only marginal relief. Venous valves may also be damaged when the valve is being reconstructed, transpositioned, or transplanted. The endothelium tissue layer of the vein may also be damaged during handling. This reduces the viability of the vein graft after implant. Another disadvantage with transplantation procedures is the need to use the patient's own vein segment in order to avoid the complications posed by rejection. In addition, the use of a patient's own vein segment predisposes that the incompetence or damage did not arise from inherited factors or diseases which will affect the transplanted valve.

Another surgical procedure involves the removal of the valve. In this procedure, the incompetent or damaged valve is completely removed. While this procedure removes any potential impediment to normal blood flow, it does not solve the backflow problem.

As an alternative to surgical intervention, drug therapy to correct venous valvular incompetence has been utilized. Currently, however, there are no effective drug therapies available.

Other means and methods for treating and/or correcting damaged or incompetent valves include utilizing xenograft valve transplantation (monocusp bovine pericardium), prosthetic/bioprosthetic heart valves and vascular grafts, and artificial venous valves. The use of xenograft valve transplantation is still in the experimental stages. In addition, after a given amount of time, it has been found that luminal deposits of fibrous material develops. Prosthetic heart valves are usually made from porcine valves and porcine heart valves have a geometry unsuitable as a replacement for venous valves. These types of valves are also generally larger than venous valves, and include valve leaflets generally thicker and stiffer than the leaflets of venous valves. The thicker heart valve leaflets require a greater opening pressure. The greater required opening pressure makes such valves unsuitable for the venous system. Artificial venous valves are known in the art. For example, U.S. Pat. No. 5,358,518 to Camilli discloses an artificial venous valve. The device comprises a hollow elongated support and a plate mounted therein. The plate is moveably mounted such that when in a first position, blood flows through the valve and when in a second position, blood cannot flow through the valve. A pressure differential drives the plate. Although the device is made from biocompatible materials, the use of non-physiological materials in this type of pivoting plate arrangement increases the risk of hemolysis and/or thrombosis.

SUMMARY OF THE INVENTION

The stent-based venous valve of the present invention provides a means for overcoming the difficulties associated with the treatments and devices as briefly described above.

In accordance with one aspect, the present invention is directed to an artificial venous valve. The artificial venous valve comprises a stent formed from a lattice of interconnected elements and having a substantially cylindrical configuration with first and second open ends. One or more of the elements are deformed inwardly out of the circumferential plane. The artificial venous valve also comprises a biocompatible material attached to the one or more elements thereby forming one or more valve flaps.

In accordance with another aspect, the present invention is directed to an artificial venous valve. The artificial venous valve comprises a self-expanding stent formed from a lattice of interconnected elements and having a substantially cylindrical configuration with first and second open ends and a compressed diameter for insertion into a vessel and an expanded diameter for deployment into the vessel. The one or more of the elements are deformed out of the circumferential plane at a first angle when the self-expanding stent is at its compressed diameter and at a second angle when the self-expanding stent is at its expanded diameter. The second angle is greater than the first angle. The artificial venous valve also comprises a biocompatible material attached to the one or more elements thereby forming one or more valve flaps.

The stent-based venous valve of the present invention utilizes a modified self-expanding stent to create an effective artificial venous valve. One or more elements comprising the framework of the self-expanding stent are deformed out of the circumferential plane and towards the center of the stent and a lightweight, biocompatible fabric is attached thereto. The attachment of the fabric to the elements creates flaps which function to regulate the flow of blood in the veins into which it is positioned. The slightly higher blood pressure upstream of the stent easily opens the flaps and allows the blood to flow through. In the absence of a pressure differential, the flaps return to their normally closed position, thereby substantially preventing the backflow of blood.

The stent-based venous valve of the present invention may be percutaneously delivered to the venous sub-system by releasing it from a catheter to assist or replace deteriorating natural venous valves by allowing flow towards the heart and preventing backflow. Since the venous valve is percutaneously delivered, the whole procedure is minimally invasive. The stent-based venous valve creates very little resistance in the vessel and offers minimal complication risks. In addition, since the stent-based venous valve utilizes modified existing technology, physicians will be more comfortable performing the valve replacement procedure.

The stent-based venous valve of the present invention may be more cost effectively manufactured by utilizing existing manufacturing techniques that are currently used for the manufacture of stents with only slight modification. Accordingly, high quality, reliable venous valves may be easily manufactured at relatively low cost.

BRIEF DESCRIPTION OF THE DRAWINGS

The foregoing and other features and advantages of the invention will be apparent from the following, more particular description of preferred embodiments of the invention, as illustrated in the accompanying drawings.

DETAILED DESCRIPTION OF THE PREFERRED EMBODIMENTS

The stent-based venous valve of the present invention comprises a self-expanding stent in which one or more of its elements are deformed inwardly towards its center, and a biocompatible fabric which is attached to the one or more deformed elements. With no pressure differential between the upstream and downstream ends of the venous valve, the fabric covered elements substantially occlude the lumen. When there is a pressure differential, albeit slight, due to the pumping of the heart, the fabric covered elements open easily and allow blood to flow therethrough with substantially no backflow. Given the design of the circulatory system, the pressure in the upstream portion of the venous system should always be higher than the pressure downstream. The venous valve is percutaneously delivered to the venous system by releasing it from a delivery catheter and functions to assist or replace incompetent or damaged natural venous valves by allowing normal blood flow and preventing or reducing backflow. Although any self-expanding stent may be utilized in constructing the venous valve, for ease of explanation, the exemplary embodiments described below will be with reference to one particular self-expanding stent design as set forth herein.

Figure 1:
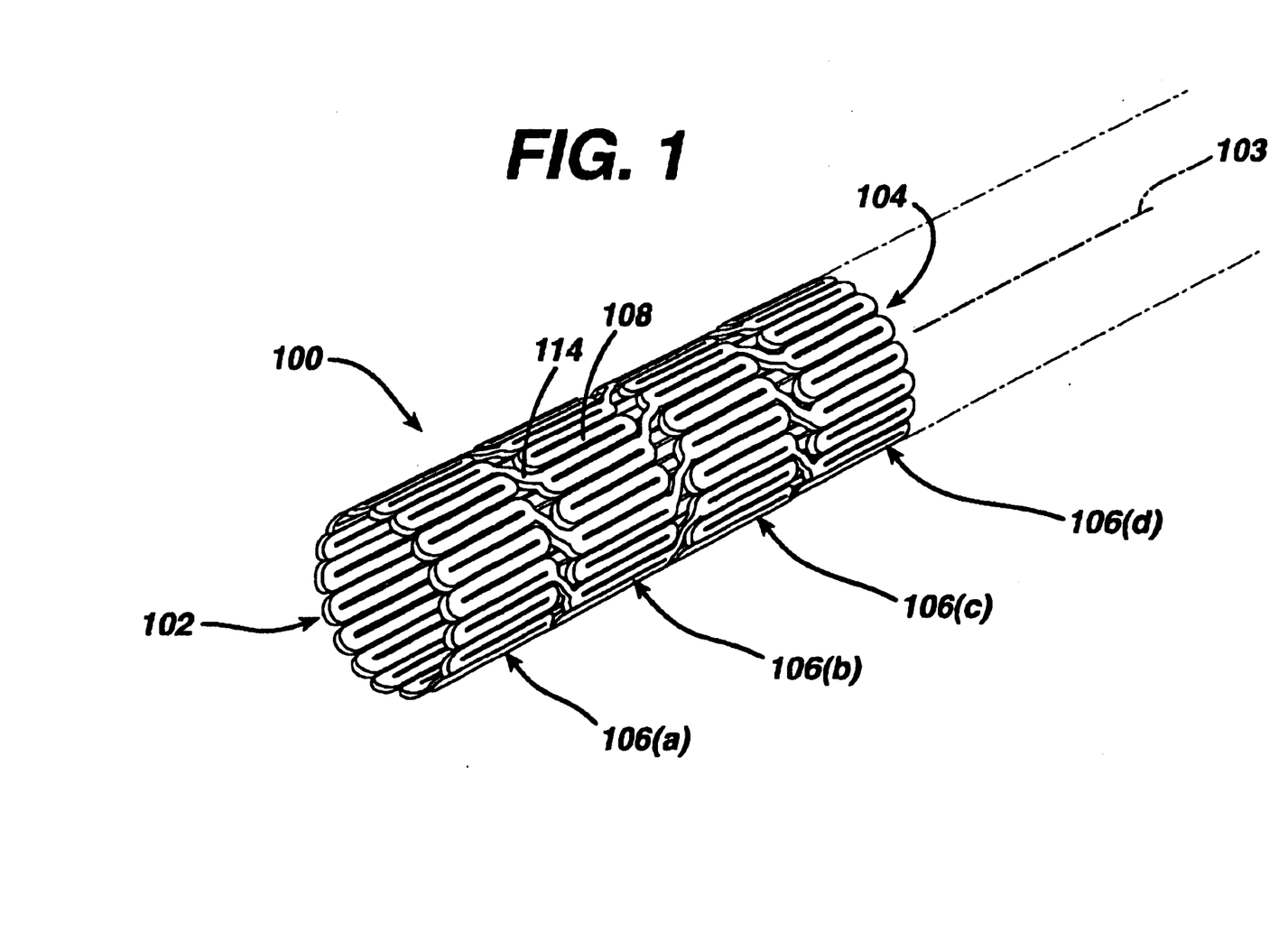
FIG. 1 is a perspective view of a stent in a compressed state in accordance with the present invention.
Figure 2:
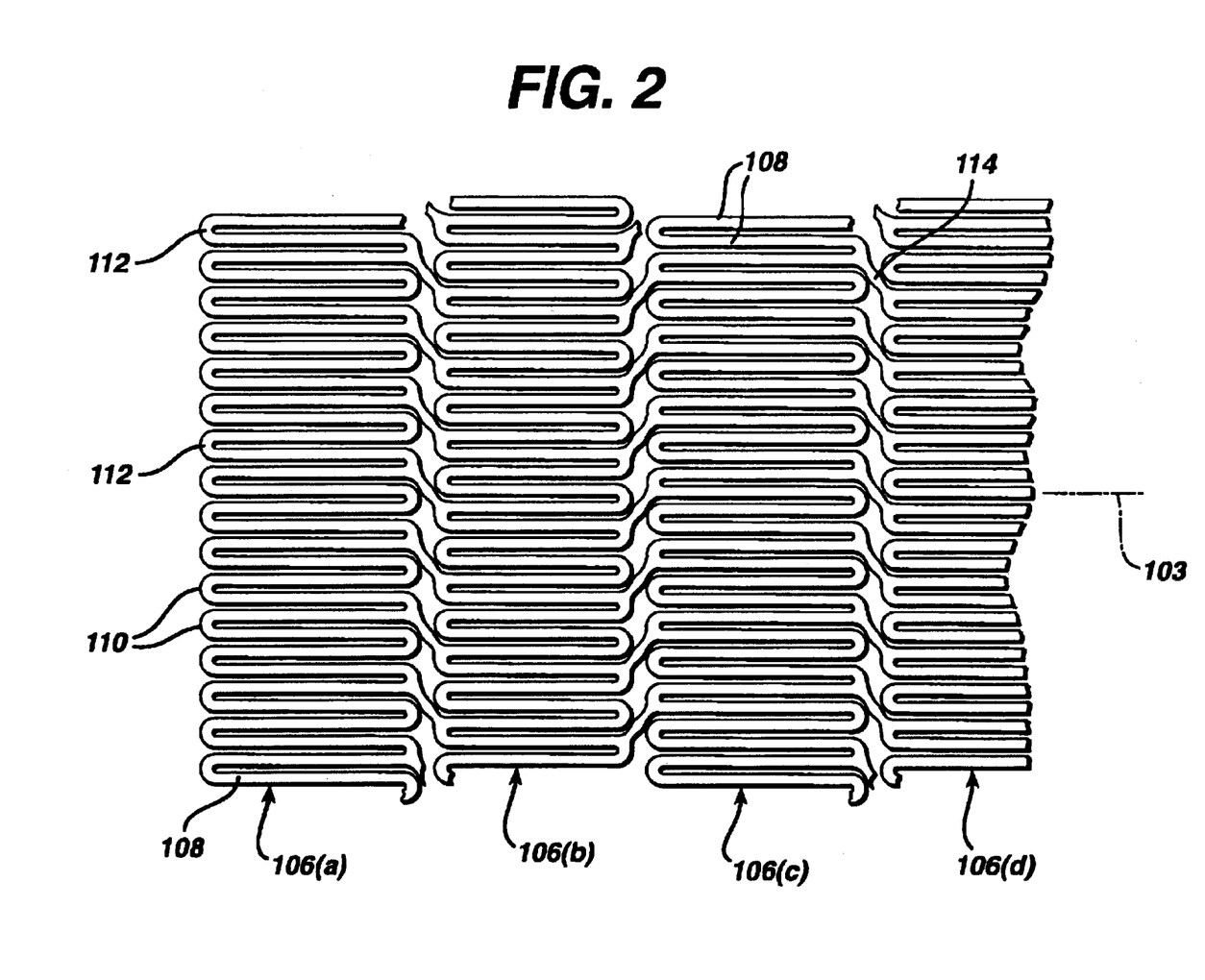
FIG. 2 is a sectional, flat view of the stent illustrated in FIG. 1.
Figure 3:
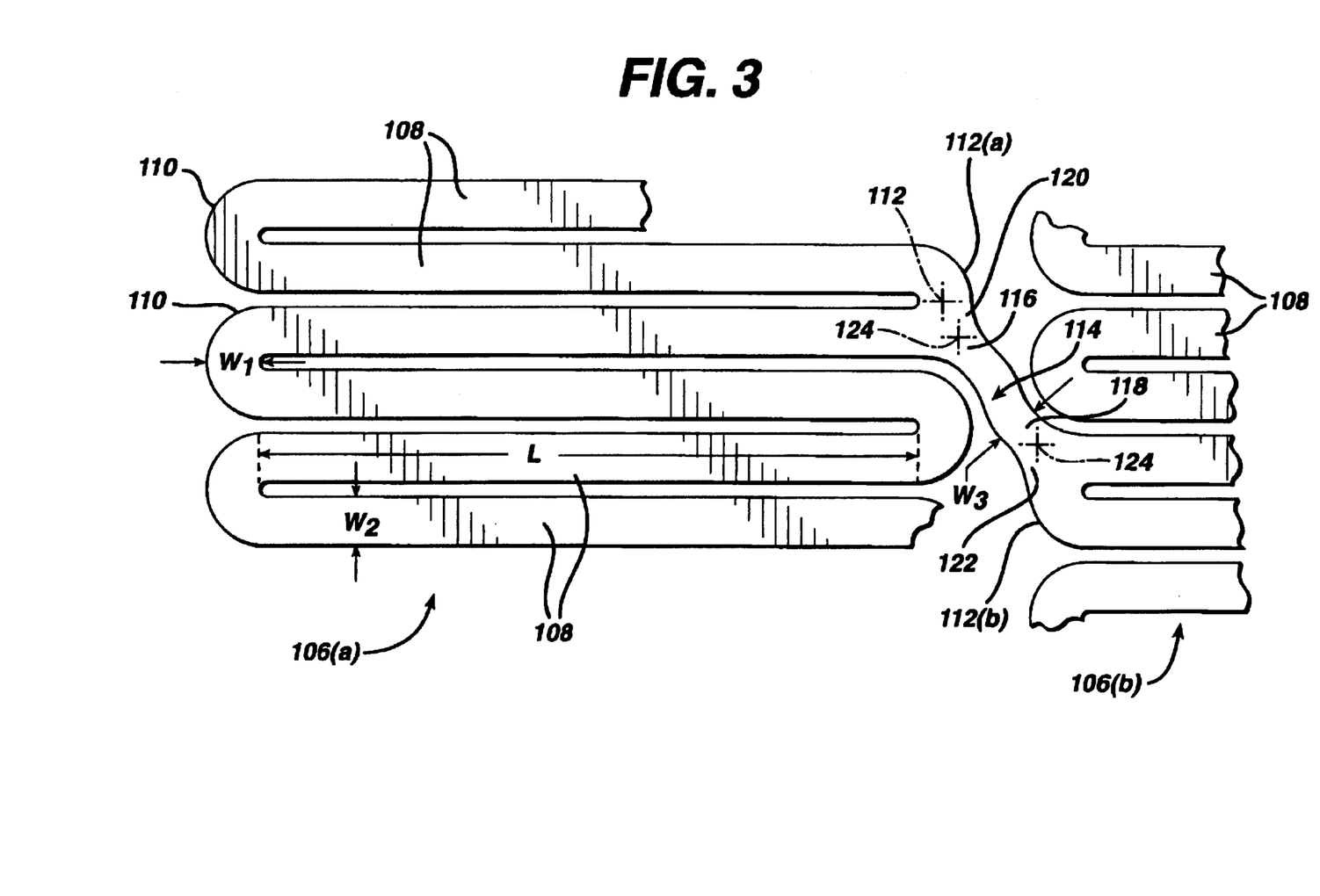
FIG. 3 is an enlarged view of the section of the stent illustrated in FIG. 2.

Referring to FIGS. 1–3, there is illustrated an exemplary stent 100 in accordance with the present invention. FIGS. 1–3 illustrate the stent 100 in its unexpanded or compressed state. In a preferred embodiment, the stent 100 comprises a superelastic alloy such as Nitinol. More preferably, the stent 100 is formed from an alloy comprising from about 50.5 to 60.0 percent Ni by atomic weight and the remainder Ti. Even more preferably, the stent 100 is formed from an alloy comprising about 55 percent Ni and about 45 percent Ti. The stent 100 is preferably designed such that it is superelastic at body temperature, and preferably has an Af temperature in the range from about 24° C. to about 37° C. The superelastic design of the stent 100 makes it crush recoverable and thus suitable as a stent or frame for any number of vascular devices for different applications.

The stent 100 comprises a tubular configuration having front and back open ends 102, 104 and defining a longitudinal axis 103 extending therebetween. The stent 100 has a first diameter for insertion into a patient and navigation through the vessels and a second diameter for deployment into the target area of a vessel with the second diameter being greater than the first diameter. The stent 100 comprises a plurality of adjacent hoops 106(a)–(d) extending between the front and back ends 102, 104. The hoops 106(a)–(d) include a plurality of longitudinally arranged struts 108 and a plurality of loops 110 connecting adjacent struts 108. Adjacent struts 108 are connected at opposite ends so as to form a substantially S or Z shape pattern. The plurality of loops 110 have a substantially semi-circular configuration and are substantially symmetric about their centers 112.

The stent 100 further comprises a plurality of bridges 114, which connect adjacent hoops 106(a)–(d). The details of the bridges 114 are more fully illustrated in FIG. 3. Each bridge comprises two ends 116, 118. One end of each bridge 114 is attached to one loop 110 on one hoop 106(a) and the other end of each bridge 114 is attached to one loop 110 on an adjacent hoop 106(b). The bridges 114 connect adjacent hoops 106(a)–(d) together at bridge to loop connection regions 120, 122. For example, bridge end 116 is connected to loop 110(a) at bridge to loop connection region 120, and bridge end 118 is connected to loop 110(b) at bridge to loop connection region 122. Each bridge to loop connection region includes a center 124. The bridge to loop connection regions 120, 122, are separated angularly with respect to the longitudinal axis 103 of the stent 100. In other words, and as illustrated in FIG. 3, a straight line drawn between the center 124 of each bridge to loop connection region 120, 122 on a bridge 114 would not be parallel to the longitudinal axis 103 of the stent 100.

The above-described geometry better distributes strain throughout the stent 100, prevents metal to metal contact where the stent 100 is bent, and minimizes the opening between the features of the stent 100; namely, struts 108, loops 110 and bridges 114. The number of and nature of the design of the struts, loops and bridges are important design factors when determining the working properties and fatigue life properties of the stent. It was previously thought that in order to improve the rigidity of the stent, struts should be large, and thus there should be fewer struts per hoop. However, it is now known that stents having smaller struts and more struts per hoop improve the construction of the stent and provide greater rigidity. Preferably, each hoop has between twenty-four (24) to thirty-six (36) or more struts. It has been determined that a stent having a ratio of number of struts per hoop to strut length which is greater than four hundred has increased rigidity over prior art stents which typically have a ratio of under two hundred. The length of a strut (L) is measured in its compressed state parallel to the longitudinal axis 103 of the stent 100 as illustrated in FIG. 3.

Figure 4:
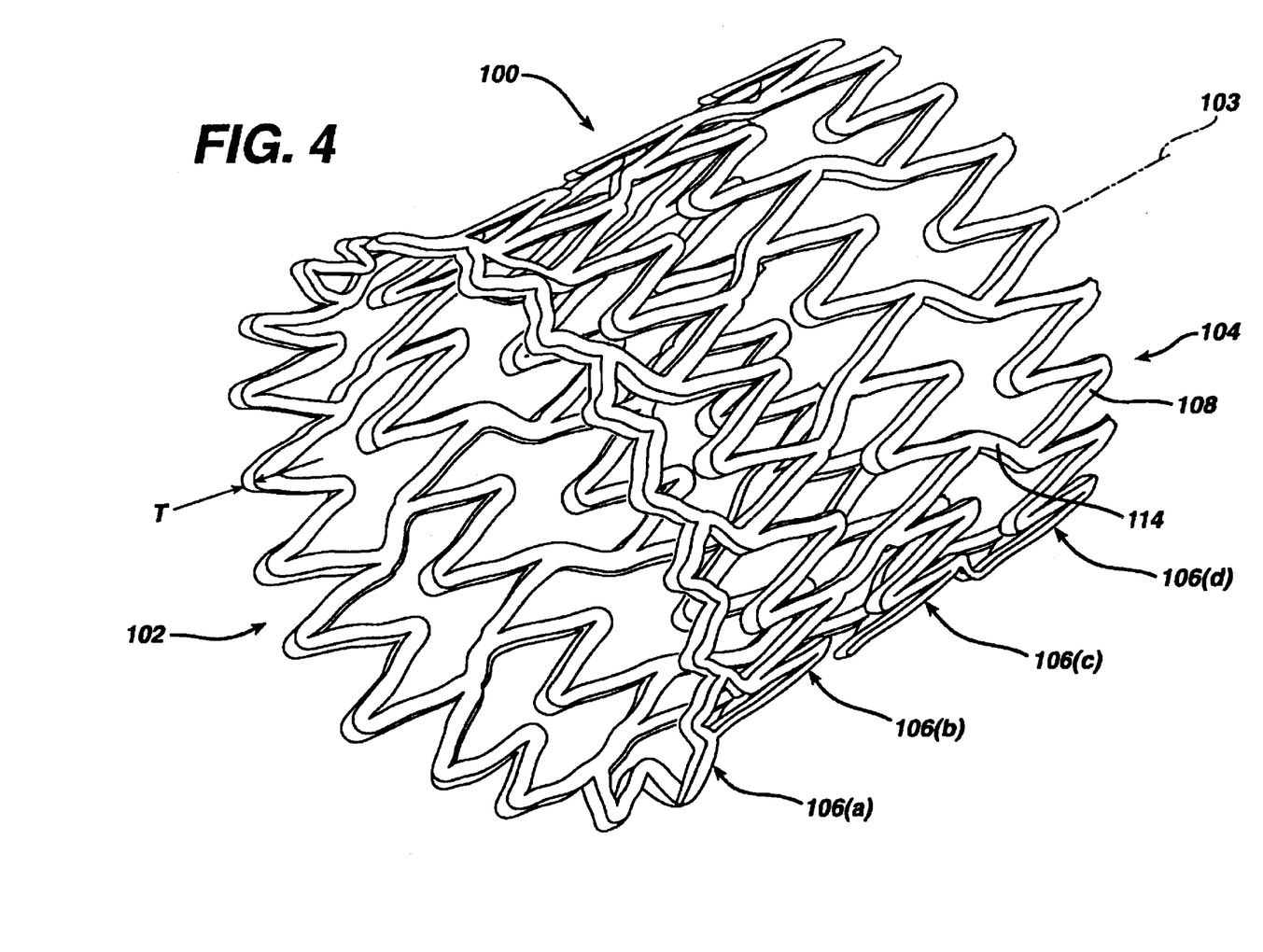
FIG. 4 is a perspective view of the stent illustrated in FIG. 1 in its expanded state.

FIG. 4 illustrates the stent 100 in its expanded state. As may be seen from a comparison between the stent 100 illustrated in FIGS. 1–3 and the stent 100 illustrated in FIG. 4, the geometry of the stent 100 changes quite significantly as it is deployed from its unexpanded state to its expanded state. As a stent undergoes diametric change, the strut angle and strain levels in the loops and bridges are affected. Preferably, all of the stent features will strain in a predictable manner so that the stent is reliable and uniform in strength. In addition, it is preferable to minimize the maximum strain experienced by the struts, loops and bridges since Nitinol properties are more generally limited by strain rather than by stress.

In trying to minimize the maximum strain experienced by the features of the stent, the present invention makes use of structural geometries which distribute strain to areas of the strut which are less susceptible to failure than others. For example, one of the more vulnerable areas of the stent is the inside radius of the connecting loops. In going from its unexpanded state to its expanded state the connecting loops of the stent undergo the most deformation of all the stent features. The inside radius of the loop would normally be the area with the highest level of strain on the stent. This area is also critical in that it is usually the smallest radius on the stent. Stress concentrations are generally minimized by maintaining the largest radii possible. Similarly, it is preferable to minimize local strain concentrations on the bridge and bridge connection points. One way to accomplish this is to utilize the largest possible radii while maintaining feature widths, which are consistent with applied forces. Another consideration is to minimize the maximum open area of the stent. Efficient utilization of the original tube from which the stent is cut, described subsequently, increases the strength of the stent and increases its ability to trap embolic material.

Many of these design objectives are accomplished in a preferred embodiment of the stent of the present invention as illustrated in FIGS. 1–3. As seen from these figures, the most compact designs, which maintain the largest radii at the loop to bridge connections, are non-symmetric with respect to the centerline of the loop. That is, loop to bridge connection region centers 124 are off set from the center 112 of the loops 110 to which they are attached. This feature is particularly advantageous for stents having large expansion ratios, which in turn requires them to have extreme bending requirements where large elastic strains are required. Nitinol can withstand extremely high elastic strain deformation, so the above features are well suited to stents made from this alloy. Therefore, this design feature allows for maximum utilization of the properties of Nitinol to enhance stent radial strength, improve stent strength uniformity and improve stent fatigue life by minimizing local strain levels. In addition, this design feature allows for smaller open areas which enhance entrapment of embolic material and improve stent opposition in irregular vessel wall shapes and curves.

As illustrated in FIG. 3, the stent 100 comprises loops 110 each having a width, W1, as measured at its center 112 and parallel to axis 103 (illustrated in FIGS. 1 and 2), which is greater than the width, W2, of each of the struts 108, as measured perpendicular to the axis 103. In a preferred embodiment, the loops 110 have a variable thickness wherein they are thicker at their centers 64. This configuration increases strain deformation at the strut and reduces the maximum strain levels at the extreme radii of the loop. This reduces the risk of stent failure and allows for maximization of the radial strength properties of the stent. This feature is particularly advantageous for stents having large expansion ratios, which in turn requires them to have extreme bending requirements where large elastic strains are required.

As mentioned above, as a stent undergoes diametric change, strut angle and loop strain is affected. Given that the bridges connect loops on adjacent hoops, the bridges are affected by the application of a torque anywhere along the length of the stent. If the bridge design is duplicated around the stent perimeter, the displacement causes a rotational shifting of the two loops connected by each bridge. If the bridge design is duplicated throughout the stent, this shift will occur down the length of the stent. This is a cumulative effect as one considers rotation of one end with respect to the other, for example, upon deployment. When a strut is loaded into a delivery system, the stent may be twisted, thereby causing the above-described rotational shifting. Typically, stent delivery systems deploy the distal end of the stent first and then allow the proximal end to expand. It would be undesirable to allow the distal end of the stent to anchor into the vessel wall while holding the remainder of the stent fixed and then deploying the proximal end of the stent thereby potentially causing the proximal end to rotate as it expands and unwinds. Such rotation may cause damage to the vessel.

In the exemplary embodiment described herein, the above-described problem is minimized by mirroring the bridge geometry longitudinally down the stent. Essentially, by mirroring the bridge geometry longitudinally along the stent, the rotational shift of the S-shaped sections may be made to alternate which will minimize large rotational changes between any two points on a given stent during deployment or constraint. As illustrated in FIG. 2, the bridges 114 connecting hoop 106(b) to hoop 106(c) are angled upwardly from left to right, while the bridge 114 connecting hoop 106(c) to hoop 106(d) are angled downwardly from left to right. This alternating pattern is repeated down the length of the stent. This alternating pattern of bridge shapes improves the torsional characteristics of the stent so as to minimize any twisting or rotation of the stent with respect to any two hoops. This alternating bridge shape is particularly beneficial if the stent starts to twist in vivo. Alternating bridge shapes tend to minimize this effect. The diameter of a stent having bridges which are all shaped in the same direction will tend to grow if twisted in one direction and shrink if twisted in the other direction. With alternating bridge shapes, this effect is minimized and localized.

Preferably, stents are laser cut from small diameter tubing. For prior art stents, this manufacturing process leads to designs with features having axial widths which are larger than the tube wall thickness from which the stent is cut. When the stent is compressed, most of the bending occurs in the plane that is created if one were to cut longitudinally down the stent and flatten it out. However, for the individual bridges, loops and struts with widths greater than their thicknesses have a greater resistance to this in-plane bending than they do to out-of-plane bending. Given this, the bridges and struts tend to twist so that the stent as a whole can bend more easily. This twisting is essentially a buckling which is unpredictable and can cause potentially high strain. However, in a preferred embodiment of the present invention as illustrated in FIG. 3, the widths of the struts (W2), loops (W1) and bridges (W3) are equal to or less than the wall thickness of the tube from which the stent is cut. Therefore, substantially all bending, and therefore, all strains are out-of-plane. This minimizes twisting of the stent, which minimizes or eliminates buckling and unpredictable strain conditions.

Figure 5:
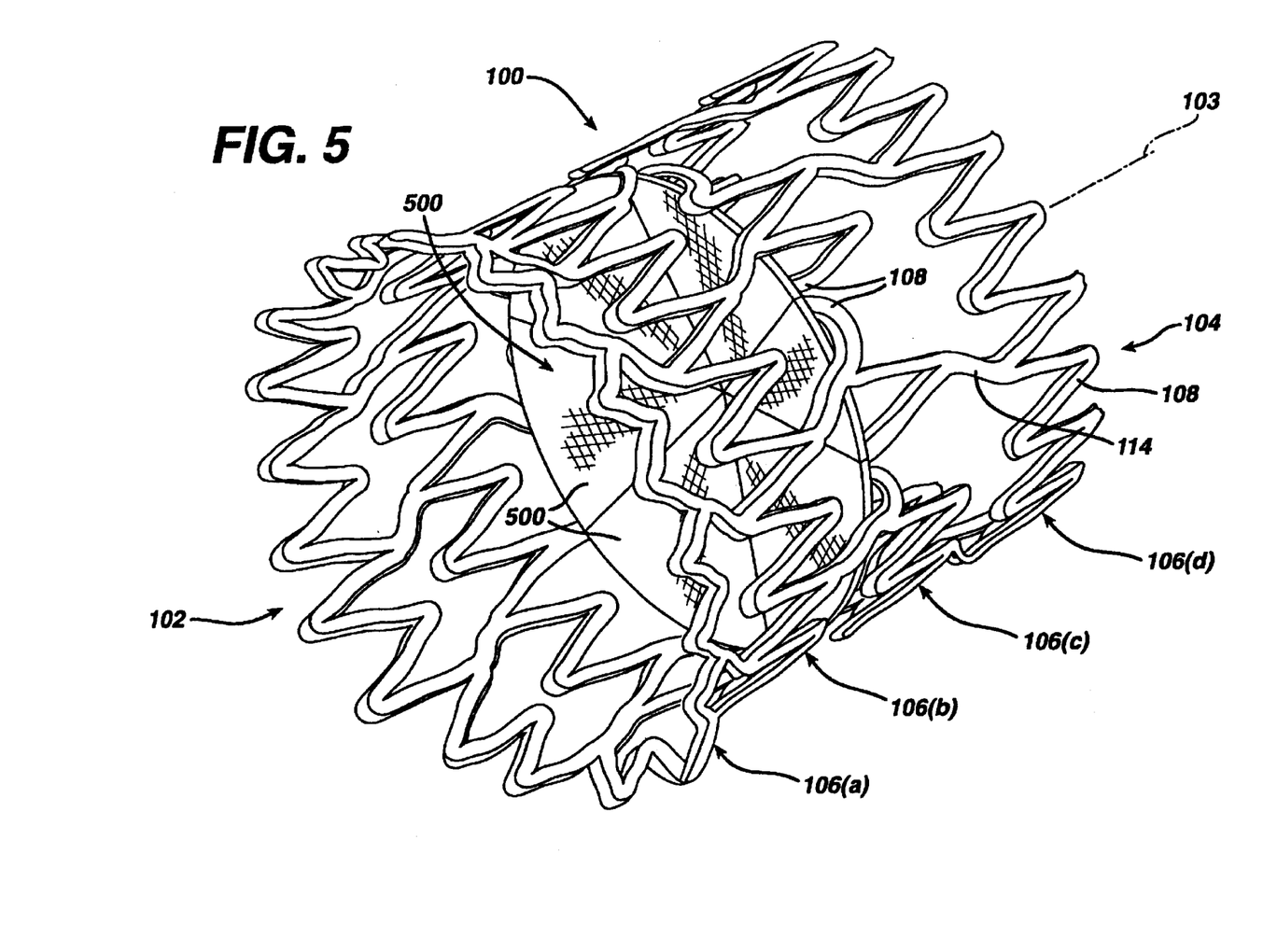
FIG. 5 is a perspective view of the stent-based venous valve in accordance with the present invention.

As briefly described above, the stent-based venous valve of the present invention comprises a self-expanding stent in which one or more of its elements are deformed inwardly towards its center, and a biocompatible fabric which is attached to the one or more deformed elements to form one or more valve flaps. In order to prevent the backflow of blood, the one or more valve flaps preferably occlude the lumen of the stent when there is no pressure differential between the upstream and downstream regions of the stent. Essentially, the occlusion of the stent lumen, and thus the vessel in which the stent is positioned, is the neutral position for the one or more valve flaps. Under normal circumstances, the pressure upstream is greater than the pressure downstream due to the nature of the circulatory system, as briefly described above. This pressure differential, albeit slight, easily opens the one or more valve flaps and allows the blood to flow substantially unimpeded. The one or more valve flaps may be positioned anywhere within the stent, including proximate to one of the open ends of the stent. In the exemplary embodiment illustrated in FIG. 5, the one or more valve flaps 500 are positioned substantially in the center of the stent 100 as measured along the longitudinal axis 103. It is important to note that a multiplicity of different stent designs exist and that the stent-based venous valve may be constructed utilizing any of these stents.

Figure 6:
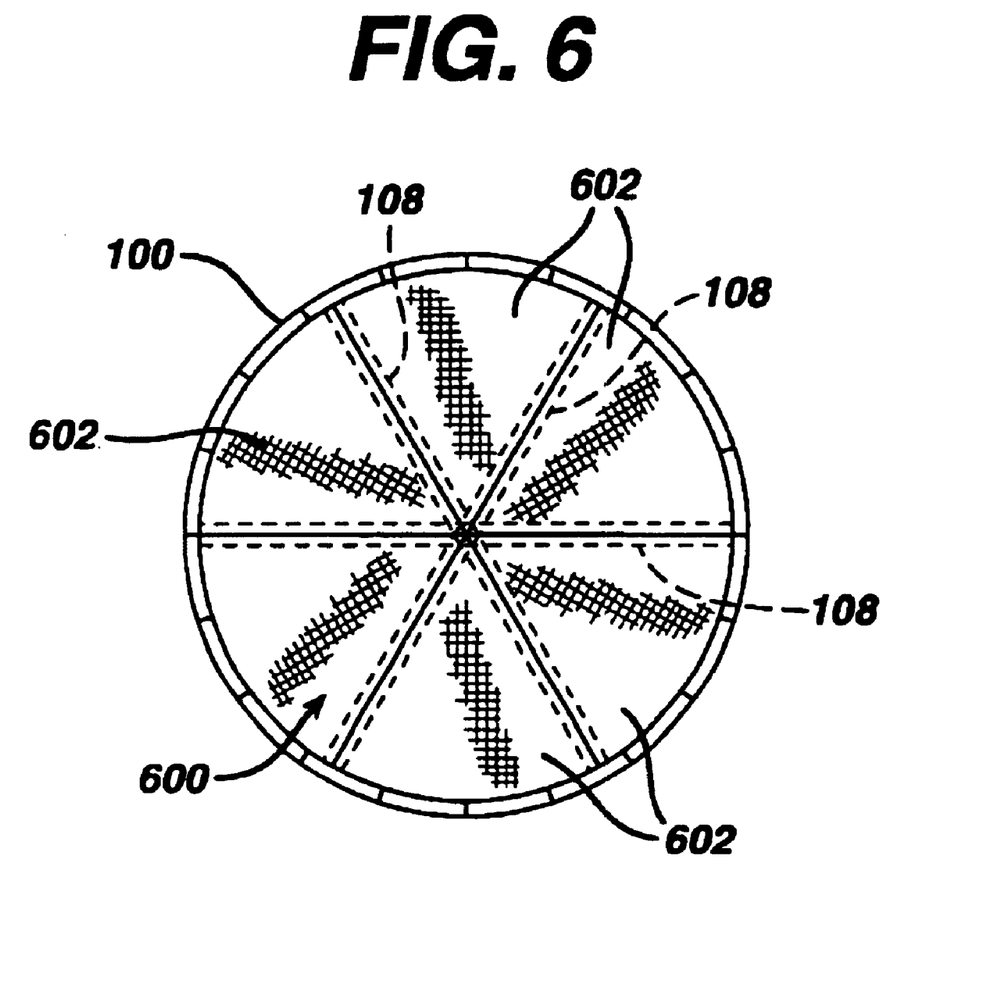
FIG. 6 is an end view of the stent-based venous valve in accordance with the present invention.

Referring to FIG. 6, there is illustrated an end view of the stent-based venous valve 600 of the present invention. Any of the elements comprising the stent 100 may be deformed inwardly to form the frame or support structure of the one or more valve flaps. For example, the bridges 114, struts 108 and/or loops 110 may be utilized. In the exemplary embodiment illustrated in FIG. 6, the struts 108 are utilized. In order to deform the struts 108 out of the circumferential plane, the struts 108 have to be severed. The length of the deformed strut 108 and thus the point at which it is severed along its length depends on a number of factors, including the diameter of the stent 100, the number of deformed struts 108 comprising the frame of a valve flap and the number of valve flaps. With respect to the diameter factor, the length of the deformed strut 108 may vary with stent 100 diameter in order to provide sufficient support for the one or more valve flaps. For example, as the diameter of the stent 100 increases, the length of the deformed strut 108 should also preferably increase to compensate for the increased surface area of the one or more valve flaps. With respect to the number of deformed struts 108 comprising each frame of the one or more valve flaps and the number of valve flaps, it is obvious that the length of the deformed struts 108 will vary depending on the design and number of the one or more valve flaps. For example, if triangularly shaped valve flaps are utilized, two deformed struts 108 may be utilized as the legs of the triangularly shaped valve flap, and the length of the deformed struts 108 should be substantially equal to the radius of the stent 100 so that the apex of each triangularly shaped valve flap meets and is supported in the center of the lumen in order to substantially occlude the lumen in the absence of a pressure differential as described above.

Figure 7:
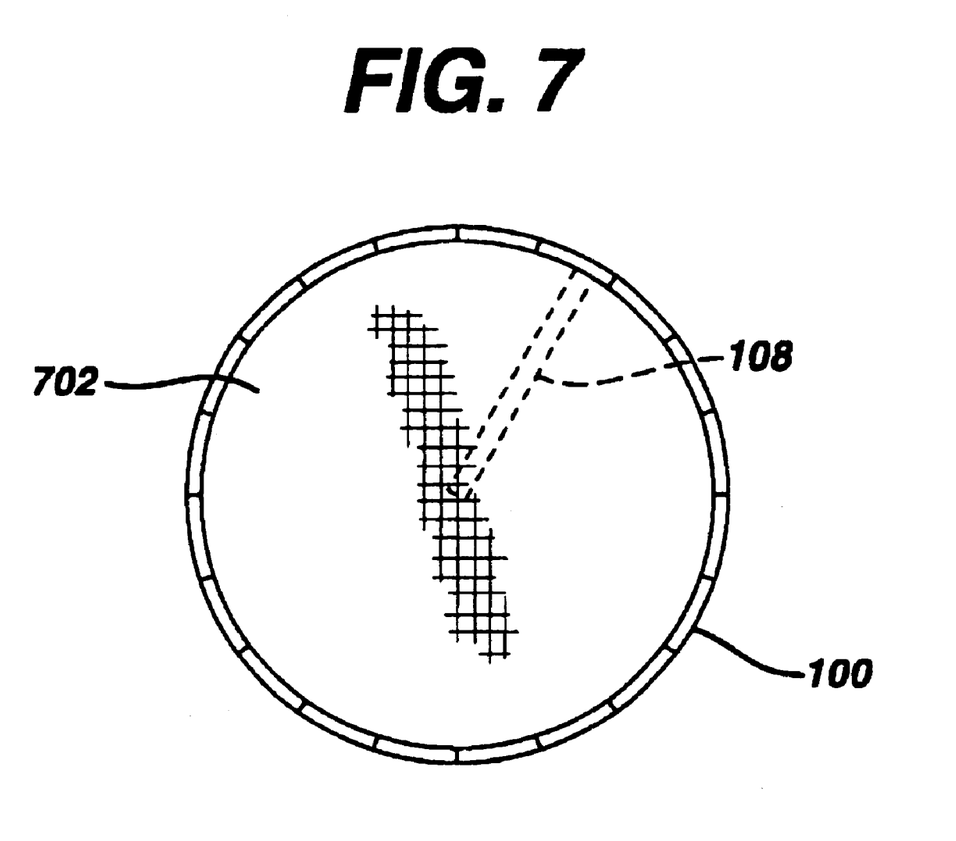
FIG. 7 is an end view of the stent-based venous valve having a single valve flap in accordance with the present invention.
Figure 8:
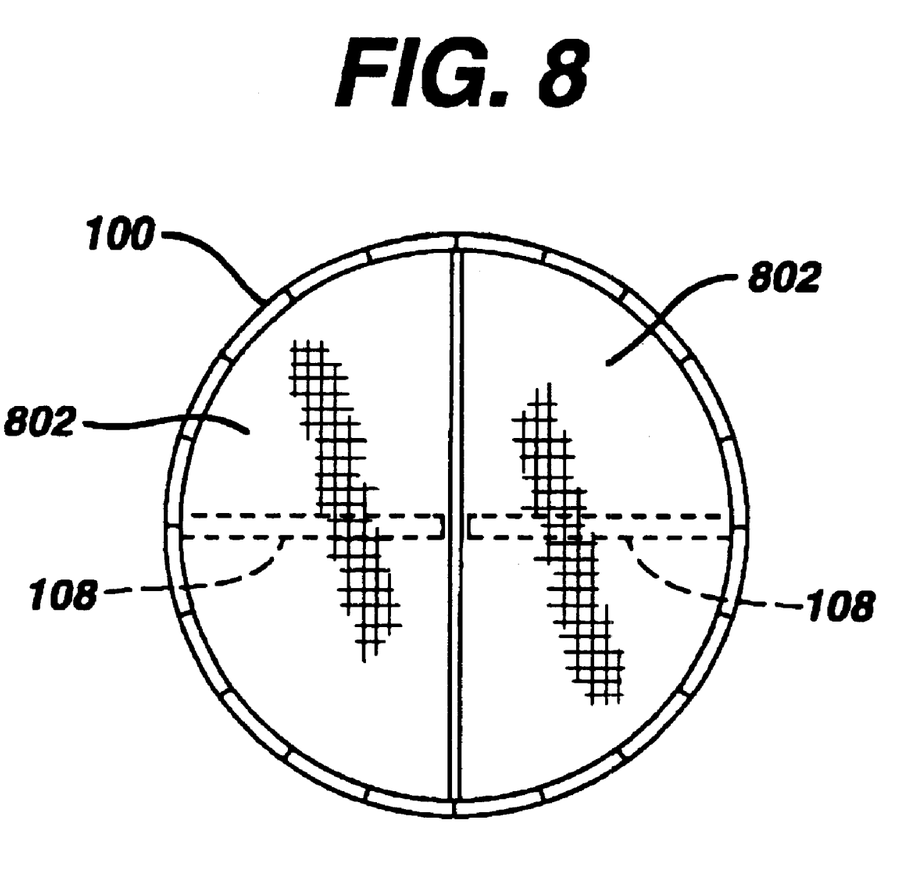
FIG. 8 is an end view of the stent-based venous valve having two valve flaps in accordance with the present invention.

Any number of valve flaps having any number of configurations may be utilized in the stent-based venous valve of the present invention. In one exemplary embodiment, a single valve flap may be formed utilizing one or more deformed struts 108. For example, as illustrated in FIG. 7, a single deformed strut 108 may support a substantially circularly shaped section 702 of biocompatible fabric having a diameter substantially equal to the inner diameter of the stent 100. In another exemplary embodiment, as illustrated in FIG. 8, two valve flaps 802 may be formed utilizing one or more deformed struts 108. For example, back to back substantially D-shaped valve flaps may be utilized. In the exemplary embodiment illustrated in FIG. 6, six substantially triangularly shaped valve flaps 602 are utilized. The valve flaps 602 cannot have a true triangular shape because the base of each valve flap 602 is curved to fit the circumferential arc of the stent 100. Each valve flap 602 comprises two deformed struts 108, which are angled to form the legs of the valve flap 602. Given that there are six valve flaps 602, each comprising two deformed struts 108, a total of twelve deformed struts 108 are utilized. Each of the deformed struts 108 extends from the wall of the stent 100 towards the center of the lumen such that their distal ends are proximate one another. Each of the deformed struts 108 may extend from the circumferential plane of the stent 100 substantially perpendicular thereto, or at any other angle as long as the distal ends terminate proximate to the center of the lumen. As stated above, the deformed struts 108 should be long enough to provide sufficient support for the valve flaps 602. Accordingly, depending on the angle, the length of each of the deformed struts 108 may vary. If any other angle other than ninety degrees is utilized, the deformed struts will be pointing more towards one of the open ends 102, 104 of the stent 100 than the center of the stent 100. In a preferred embodiment, the deformed struts 108 and thus the valve flaps 602, extend at an angle in the range from about twenty degrees to about seventy degrees. The end of the stent 100 towards which the deformed struts 108 are angled is the downstream end of the stent-based venous valve. With the angle of the deformed struts 108 in the above range, the valve flaps 602 easily open under the pressure differential existing in the venous position of the circulatory system. Accordingly, the downstream end of the stent-based venous valve 602 should be positioned at the downstream end of the section of the vein where the stent-based venous valve 600 is to be positioned.

In addition to the above described advantage of angling the valve flaps 602, the angling of the valve flaps 602 allows the stent-based venous valve 600 to be compressed for delivery. When the stent-based venous valve 600 is collapsed for insertion into the vein of a patient, the valve flaps 602 simply deflect further along the longitudinal axis in the direction in which they are angled, thereby reducing the angle of the deformed struts 108. When the stent-based venous valve 600 is expanded during deployment, the valve flaps 602 return to an angle in the range set forth above.

In order to maintain the strength of the deformed struts 108 comprising the frames of the valve flaps 602 while affording adequate fatigue lifetime, it is preferable to have struts 108 with variable strut width, i.e., zones of reduced stiffness where the strut 108 begins to bend out of the circumferential plane of the stent 100. The struts 108 may be deformed at any time during the stent manufacturing process described subsequently, or upon completion of the stent manufacturing process as part of a separate valve manufacturing process.

Each of the valve flaps 602 comprise the frame formed from the deformed elements 108 as described above, and a biocompatible material attached thereto. Any suitable lightweight, strong, fluid impervious, biocompatible material may be utilized. In a preferred embodiment, a Dacron® or Teflon® fabric may be utilized. The fabric may be attached in any suitable manner and by any suitable means. For example, the fabric may be removably attached or permanently attached to the deformed elements. The fabric may be attached to the elements utilizing sutures, staples, chemical/heat bonding and/or adhesive. In a preferred embodiment, the fabric is attached utilizing sutures.

It may be necessary to include anchors to prevent migration of the stent-based venous valve due to the weight of the blood upstream of the valve flaps 602. Such anchors would be incorporated by bending metallic features of the stent 100 outwards from the circumferential plane of the stent 100. In other words, one or more of the elements comprising the stent 100 may be deformed outwardly from the stent 100 and formed into hooks or barbs which may be made to engage the endoluminal surface of the host vein.

Stents may be manufactured from a number of different materials and utilizing a number of different processes/techniques. The nickel-titanium self-expanding stent utilized in the stent-based venous valve of the present invention is preferably manufactured utilizing the materials and processes as generally described below. Sections of Nitinol tubing are cut into stents by machines in which the tubing is secured into position while a laser cuts predetermined patterns, such as the patterns described above, out of the tubing. Essentially, the machines are adapted to hold the tubing at its open ends while a cutting laser, preferably under microprocessor control, cuts the predetermined pattern. The pattern dimensions, geometries and associated laser positioning requirements are preprogrammed into a microprocessor based system, which controls all aspects of the laser cutting process. The length and the diameter of the section of tubing depends upon the size of the stent to be manufactured. Although stents are manufactured at a number of fixed dimensions, any size stent may be manufactured utilizing these techniques. Nitinol tubing is commercially available from a number of suppliers, including Nitinol Devices and Components, Freemont, Calif. Also, the cutting machines are commercially available and their use is known in the art.

Upon completion of the stent cutting step, the rough stent is treated and polished. The rough stent may be polished utilizing any number of processes well known to those skilled in the relevant art, including electropolishing and chemical polishing. The rough stents may be polished to the desired smoothness using one or more polishing techniques. The polished stent preferably has smooth surfaces with substantially no surface irregularities that might cause damage during or after deployment into a target vessel. The polished stent is then cooled until it is completely martensitic, crimped down to its unexpanded diameter and loaded into the sheath of a delivery apparatus, which are known to those of ordinary skill in the relevant art.

At various stages in the above-described manufacturing process, the stents are inspected to ensure that it meets all design requirements and all quality requirements. For example, the stents are preferably inspected/tested using a number of criteria, including pattern regularity, smoothness and dimension. A particular stent which fails to meet a certain criterion may be re-worked one or more times in order to correct the defect, depending on where in the process it failed. The number of times a stent may be reworked is limited. However, the nickel-titanium alloy itself may always be re-utilized.

In order to manufacture the stent-based venous valve of the present invention, the above process may be modified and/or further steps may be added. For example, the cutting step may be modified such that certain elements are severed and then deformed inwards in a separate step as described above. The biocompatible fabric may be attached to the deformed elements upon completion of the polishing step and preferably prior to the crimping step utilizing any of the attachment means/methods described above. The attachment of the fabric may be done manually or by an automated means. The completed stent-based venous valve may be crimped similarly to a stent and loaded into a stent delivery device. The design and operation of stent delivery systems are well known in the art.

A concern with stents in general, as well as other medical devices, is that they may exhibit reduced radiopacity under X-ray fluoroscopy. To overcome this problem, it is common practice to attach markers made from highly radiopaque materials to the stent, or to use radiopaque materials in plating or coating processes. Those materials are typically gold, platinum, or tantalum. However, due to the relative position of these materials in the galvanic series versus the position of the base metal of the stent in the galvanic series, there is a certain challenge to overcome; namely, that of galvanic corrosion.

Figure 9:
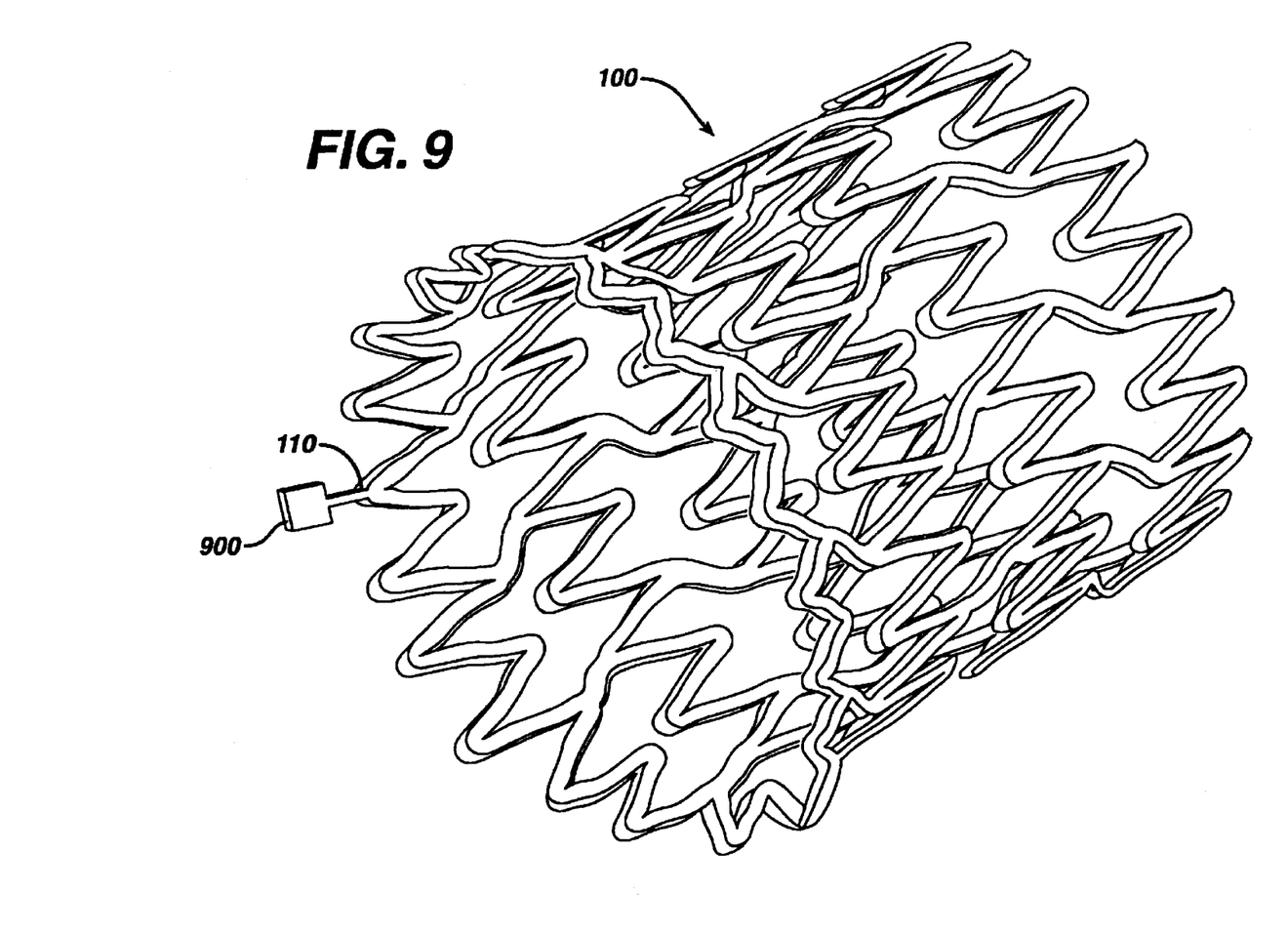
FIG. 9 is an enlarged perspective view of the end of the stent-based venous valve having a tab in accordance with the present invention.
Figure 10:
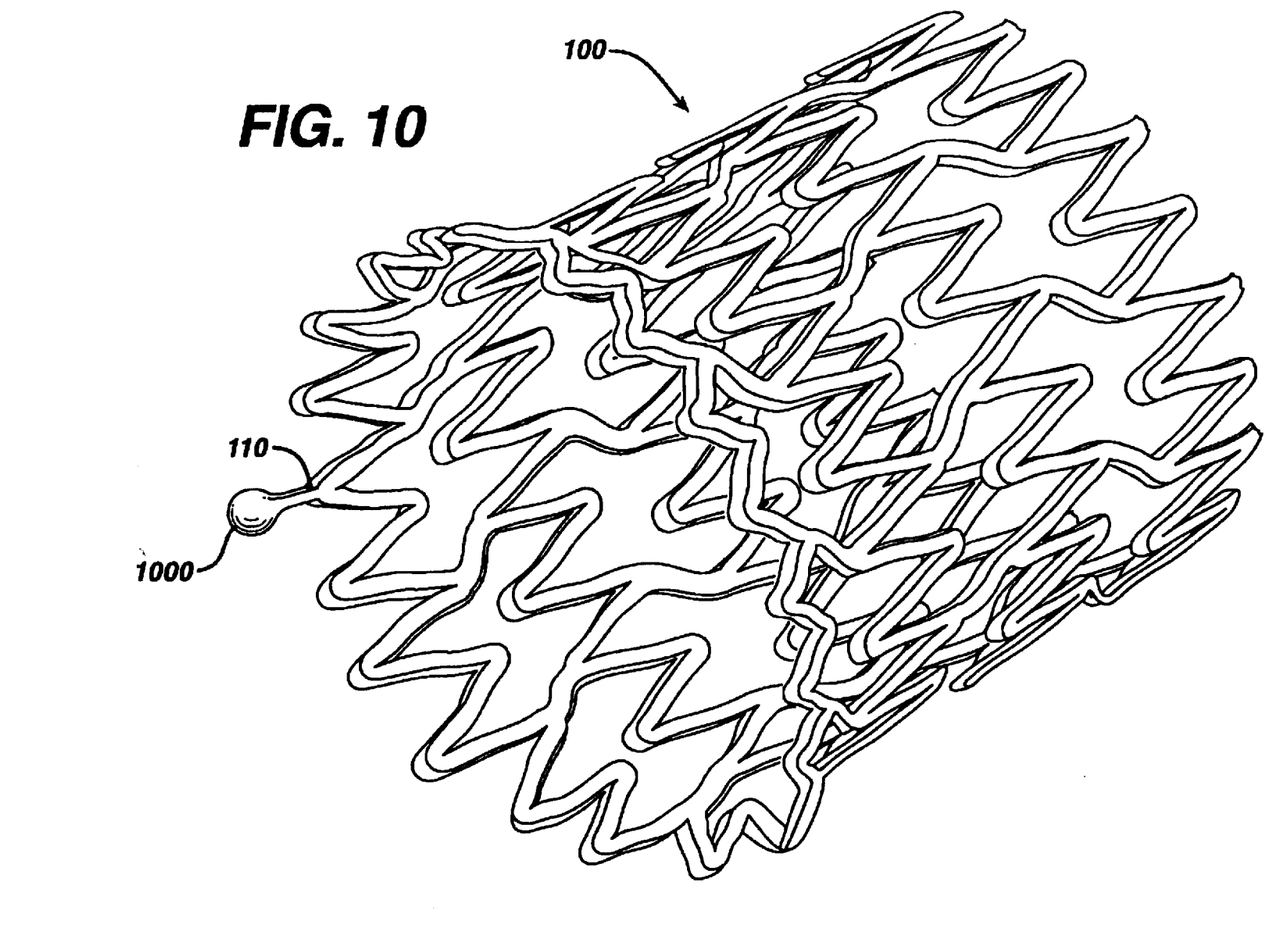
FIG. 10 is an enlarged perspective end view of the stent-based venous valve having a radiopaque marker in accordance with the present invention.

Referring to FIG. 9, there is illustrated another exemplary embodiment of the present invention. In this exemplary embodiment, the cutting pattern of the stent 100 includes at least one tab or marker 900 attached to the loops 110 at the front and back ends of the stent 100. These tabs 900 may be formed from any suitable material, and are preferably formed from a highly radiopaque material to assist in positioning the stent-based venous valve within the lumen of the vessel. In this exemplary embodiment, it is preferable to "micro-alloy" a radiopaque material like gold, platinum, tantalum, niobium, molybdenum, rhodium, palladium, silver, hafnium, tungsten or iridium with the nickel titanium at specific locations and on specific features of the stent, for example tabs 900. Once the predetermined pattern is cut into the tubular member, as described above, in a secondary process, performed in a protective atmosphere or under vacuum, the tabs 900 or other features may selectively be melted by the application of heat from a source, while a predetermined amount of the radiopaque material is added. Means for applying this heat may include devices such as lasers, induction heating, electric arc melting, resistance heating and electron beam melting, and are well known to those of ordinary skill in the art, and are commercially available. Through surface tension, the molten pool will form a sphere 1000, as illustrated in FIG. 10. The sphere 1000 remains attached to the device upon solidification. The sphere 1000 includes a micro-alloy of nickel titanium and a radiopaque alloy chosen from a group consisting of gold, platinum, tantalum, niobium, molybdenum, rhodium, palladium, silver, hafnium, tungsten and iridium, while the chemical composition of the balance of the device remains unchanged. The resulting nickel titanium alloy has a much reduced tendency to create a galvanic element with the binary nickel titanium.

Although shown and described is what is believed to be the most practical and preferred embodiments, it is apparent that departures from specific designs and methods described and shown will suggest themselves to those skilled in the art and may be used without departing from the spirit and scope of the invention. The present invention is not restricted to the particular constructions described and illustrated, but should be constructed to cohere with all modifications that may fall within the scope of the appended claims.

What is claimed is:

1. An artificial venous valve comprising:

a stent formed from a lattice of interconnected elements and having a substantially cylindrical configuration with first and second open ends, wherein one or more of the elements are deformed inwardly out of the circumferential plane; and a biocompatible material attached to the one or more elements thereby forming one or more venous valve flaps.

2. The artificial venous valve according to claim 1, wherein the stent comprises:

a plurality of hoops formed from a plurality of struts connected by a plurality of loops; and a plurality of bridges connecting adjacent hoops.

3. The artificial venous valve according to claim 1, wherein the stent comprises a superelastic alloy.

4. The artificial venous valve according to claim 3, wherein the alloy comprises from about 50.5 percent to about 60 percent nickel and the remainder comprising titanium.

5. The artificial venous valve according to claim 2, wherein the one or more valve flaps each comprise two deformed elements arranged to form a substantially triangularly shaped support frame.

6. The artificial venous valve according to claim 5, wherein the deformed elements are angled towards one of the first and second open ends at an angle in the range from about twenty degrees to about seventy degrees.

7. The artificial venous valve according to claim 6, wherein the deformed elements are thinner where they are deformed out of the circumferential plane.

8. The artificial venous valve according to claim 1, wherein the one or more valve flaps are dimensioned to substantially occlude the stent when there are no differential forces acting on the valve flaps.

9. The artificial venous valve according to claim 8, comprising six valve flaps.

10. The artificial venous valve according to claim 1, wherein the biocompatible material comprises Teflon®.

11. The artificial venous valve according to claim 1, wherein the biocompatible material comprises Dacron®.

12. An artificial venous valve comprising:

a self-expanding stent formed from a lattice of interconnected elements and having a substantially cylindrical configuration with first and second ends and a compressed diameter for insertion into a vessel and an expanded diameter for deployment into the vessel, wherein the one or more of the elements are deformed inwardly out of the circumferential plane at a first angle when the self-expanding stent is at its compressed diameter and at a second angle when the self-expanding stent is at its expanded diameter, the second angle being greater than the first angle; and a biocompatible fabric attached to the one or more elements thereby forming one or more venous valve flaps.

13. The artificial venous valve according to claim 12, wherein the self-expanding stent comprises:
  a plurality of hoops formed from a plurality of struts connected by a plurality of loops; and
  a plurality of bridges connecting adjacent hoops.

14. The artificial venous valve according to claim 12, wherein the self-expanding stent comprises a superelastic alloy.

15. The artificial venous valve according to claim 14, wherein the alloy comprises from about 50.5 percent to about 60 percent nickel and the remainder comprising titanium.

16. The artificial venous valve according to claim 14, wherein the one or more valve flaps each comprise two deformed elements arranged to form a substantially triangularly shaped support frame.

17. The artificial venous valve according to claim 14, wherein the second angle is in the range from about twenty degrees to about seventy degrees.

18. The artificial venous valve according to claim 17, wherein the deformed elements are thinner where they are deformed out of the circumferential plane.

19. The artificial venous valve according to claim 12, wherein the one or more valve flaps are dimensioned to substantially occlude the stent when there are no differential forces acting on the valve flaps.

* * * * *